United States Patent
Bromfield

(10) Patent No.: US 8,610,334 B2
(45) Date of Patent: Dec. 17, 2013

(54) ULTRASONIC TORSIONAL MODE AND LONGITUDINAL-TORSIONAL MODE TRANSDUCER

(75) Inventor: George Bromfield, Salt Lake City, UT (US)

(73) Assignee: Piezo-Innovations, Salt Lake City, UT (US)

( * ) Notice: Subject to any disclaimer, the term of this patent is extended or adjusted under 35 U.S.C. 154(b) by 0 days.

(21) Appl. No.: 13/506,755

(22) Filed: May 15, 2012

(65) Prior Publication Data
US 2012/0293044 A1  Nov. 22, 2012

Related U.S. Application Data

(62) Division of application No. 12/378,974, filed on Feb. 20, 2009.

(60) Provisional application No. 61/066,800, filed on Feb. 22, 2008.

(51) Int. Cl.
*B06B 1/06*  (2006.01)

(52) U.S. Cl.
CPC .................................... *B06B 1/0611* (2013.01)
USPC ..................................... 310/323.19; 310/322

(58) Field of Classification Search
CPC ....................................................... B06B 1/0611
USPC ................................ 310/322, 323.01–323.21
See application file for complete search history.

(56) References Cited

U.S. PATENT DOCUMENTS

| | | | |
|---|---|---|---|
| 5,628,743 A | 5/1997 | Cimino | |
| 5,630,420 A | 5/1997 | Vaitekunas | |
| 5,746,756 A | 5/1998 | Bromfield | |
| 5,843,109 A | 12/1998 | Mehta | |
| 5,879,364 A | 3/1999 | Bromfield | |
| 5,889,871 A | 3/1999 | Downs | |
| 6,004,269 A * | 12/1999 | Crowley et al. | 600/439 |
| 6,166,624 A | 12/2000 | Hurst | |
| 6,585,745 B2 | 7/2003 | Cimino | |
| 7,554,343 B2 | 6/2009 | Bromfield | |
| 7,627,936 B2 | 12/2009 | Bromfield | |
| 8,033,173 B2 | 10/2011 | Ehlert | |
| 2003/0168938 A1 | 9/2003 | Wallaschek | |
| 2005/0277869 A1 | 12/2005 | Boukhny | |
| 2006/0025897 A1 | 2/2006 | Shostak | |
| 2007/0080609 A1 | 4/2007 | Johnson | |
| 2007/0106158 A1 | 5/2007 | Madan | |

OTHER PUBLICATIONS

International Search Report mailed on Nov. 17, 2009 for PCT/US09/01103, 1 page.
IPRP issued on Aug. 24, 2010 for PCT/US09/01103, 8 pages.

* cited by examiner

*Primary Examiner* — Derek Rosenau
(74) *Attorney, Agent, or Firm* — Jeffrey J. Vaitekunas

(57) ABSTRACT

The present invention relates to the design of piezoelectric transducer subassemblies and systems primarily intended for medical and dental applications. The invention also provides transducer subassemblies and systems with improved performance and a capability to operate more efficiently in torsional or a combined longitudinal-torsional mode of vibration. The invention enables the size and weight of torsional mode transducers to be reduced. Additionally, the electrical characteristics of these transducer systems are improved, thus enabling the transducer end effector to deliver more power to the operative site.

18 Claims, 17 Drawing Sheets

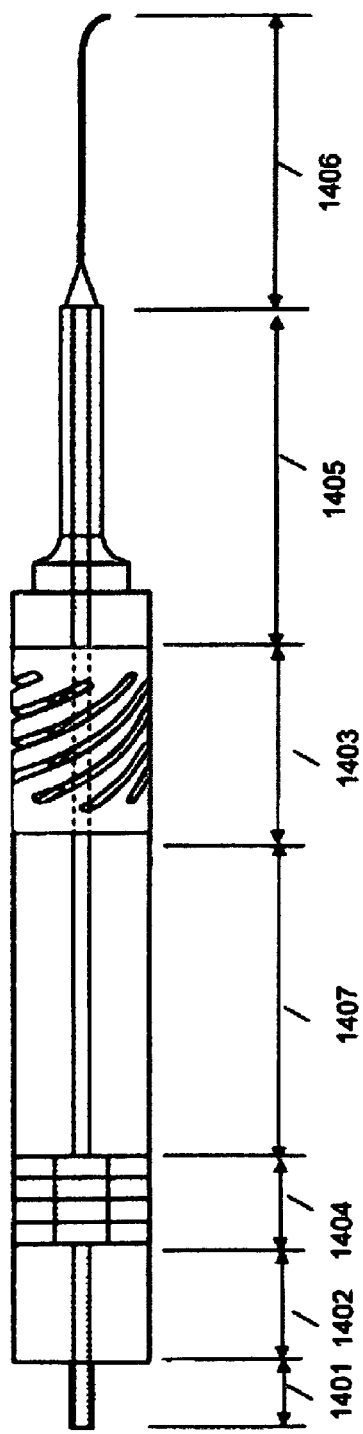
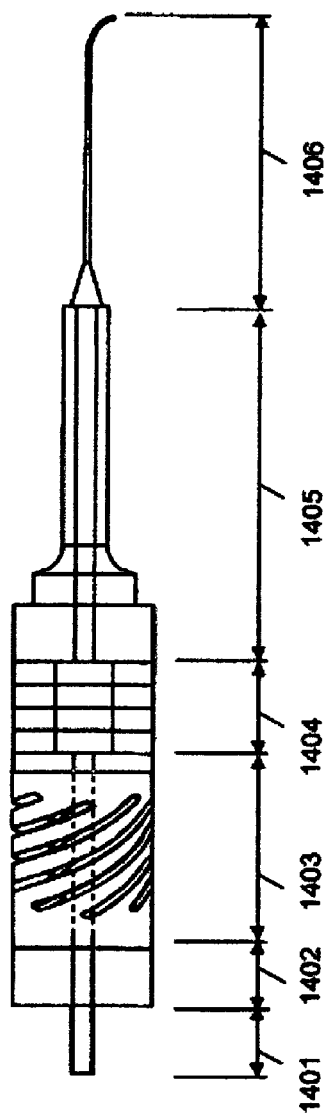
Fig. 14A Prior Art
Fig. 14b

ULTRASONIC TORSIONAL MODE AND LONGITUDINAL-TORSIONAL MODE TRANSDUCER

CROSS REFERENCE TO RELATED APPLICATIONS

This application claims priority under 35 U.S.C. §119 from Provisional Application Ser. No. 61/066,800, filed Feb. 22, 2008, the disclosure of which is incorporated herein by reference, and is a divisional of U.S. patent application Ser. No. 12/378,974, filed Feb. 20, 2009, the disclosure of which is incorporated herein by reference.

FIELD OF THE INVENTION

The invention generally relates to the field of transducers. More specifically, this invention relates to transducers configured to produce torsional motion or longitudinal-torsional motion at ultrasonic frequencies.

BACKGROUND OF THE INVENTION

Torsional mode transducer systems have been described extensively in a book entitled "Sources of High-intensity Ultrasound," Volume 2, and more specifically in Part IV, which is entitled "Torsional Mode Vibration Systems," written by A. M. Mitskevich and edited by Rozenberg in 1969. FIG. 1 illustrates one type of a torsional mode system disclosed therein. The system illustrated in FIG. 1 is normally used for welding, for example, in specialist applications such as the helium tight sealing of cans and containers. Magnetostrictive vibrators with longitudinal waveguides 101 are attached to a rod 102 with an end mass 103, wherein they excite torsional vibrations, which are transmitted to the welded parts 104 situated on the supporting platform 105. Various known modifications to this system include the replacement of the magnetostrictive vibrators with more efficient piezo-electric vibrators and the use of two vibrators in a push-pull mode. Mitskevich concludes that the system illustrated in FIG. 1 is awkward, inconvenient and extremely unsuitable from the energy point of view.

Torsional mode transducer systems that include an end effector for surgical applications, specifically for cutting and coagulating tissue have been described by Young (U.S. Pat. No. 6,425,906). The transducer system disclosed by Young is illustrated in FIG. 2. Young attempted to eliminate longitudinal motion by attaching the longitudinal transducer 202 at right angles to the torsional mode waveguide 204. The motive force for transducer 202 is provided by piezo electric drive elements 203. Young noted that the use of torsional mode vibration for ultrasonic scalpel/coagulation applications is safer because energy is absorbed into the target tissue and not transmitted along the waveguide axis into distant regions. One disadvantage of this design geometry is that it is difficult to incorporate within a slim ergonomic surgical tool that is both compact and light weight.

In addition to torsional mode transducer systems, there are longitudinal-torsional (L-T) mode transducer systems. These L-T mode transducer systems are rod systems, which, when driven in a longitudinal mode, are capable of generating a torsional vibration component by virtue of a certain inhomogeneity in the cross section of the rod. Mitskevich (cited above) has described such systems. One such device consisted of an ultrasonic horn 300, as is shown in FIG. 3. The horn, itself, is marked with gradually deepening grooves 303; these form a helix with a smooth diminishing pitch. Excitation over the frequency range 15 kHz to 21 kHz was accomplished by means of a ferrite or magnetostrictive transducer (not shown) attached by the screwed thread 301 at the proximal end of the horn. The variation in the tangential (x) and longitudinal (y) components of vibration at the distal tip of the horn 302 as a function of driving frequency is shown in FIG. 4. As can be seen in FIG. 4, the longitudinal component (y) at the distal tip of the horn 302 is reduced to zero at a frequency of 16.5 kHz resulting in a single tangential mode of vibration. FIG. 4 also shows that the tangential or torsional mode of vibration is reduced to zero at a frequency of approximately 17.8 kHz resulting in a single longitudinal mode of vibration. Additionally, the tip of the horn 302 vibrates in a combined L-T mode at frequencies other than 16.5 kHz and 17.8 kHz (see FIG. 4). For example, at a frequency of approximately 16.3 kHz the component of longitudinal vibration is similar to the component of tangential vibration. Mitskevich also describes L-T resonators made by creating an inhomogeneous cross section along the length of an otherwise uniform bar and then twisting the bar along its length. The same structure can be obtained by using a conventional twist drill or by machining the grooves into the bar.

Wuchinich (U.S. Pat. No. 6,984,220) disclosed the design of a similar longitudinal-torsional device that operates at a combined L-T resonance and is used to dissect biological tissue. The transducer and L-T resonator system disclosed by Wuchinich is reproduced in FIG. 5. The motive force for transducer 519 can be either magnetostrictive or piezoelectric and is designed to operate as a half-wave resonator. The longitudinal vibrations 523 at the distal tip of the transducer are coupled to resonator section 521 that has an inhomogeneous cross section that converts the single longitudinal motion into a combined L-T motion at the tissue contacting tip 524. The inhomogeneous cross section can be in the form of a helical spiral spring similar to that illustrated in FIG. 3.

Use of the Wuchinich design for ultrasonic handpieces used for surgical procedures such as cataract removal (phacoemulsification) and dental teeth cleaning would result in suboptimal handpiece in terms of length and weight. Typically, these handpieces operate at frequencies >28 kHz and <40 kHz. Operating above 28 kHz reduces the risk of an audible sub-harmonic frequency and operating below 40 kHz optimizes the design for maximum displacement of the end effector at the operative site. The maximum operational frequency for a medical handpiece is about 250 kHz. Designing a 28 kHz piezoelectric transducer/L-T resonator using the teachings of Wuchinich would result in a handpiece design that would have an overall length of about 200 mm (8 inches) if allowance is made for electrical connection at the proximal end of the transducer. This length is significantly longer than existing current designs and would be heavier, thus making it impractical to use for these applications.

Boukhny (U.S. Pat. No. 6,077,285) also described an apparatus for providing both longitudinal and torsional ultrasonic motion for the purpose of enhancing tissue dissection. His device utilizes separate torsional and longitudinal transducers systems to provide this motion. To obtain the desired result requires the simultaneous operation of both transducer systems. To supply the power required the use of two electrical generators, one for each of the different transducer systems. Furthermore, all such devices as described by Boukhny, whether longitudinal, transverse or torsional must be fixed within an enclosure, such as a handpiece, preferably at points where there is no motion, known as motional nodes. However, because the wavelength of torsional and longitudinal vibration is substantially different, the node or nodes for longitudinal vibration and torsional motion will be located at different points on the transducer system and other portions of other resonators attached to the transducer system. Hence, no true motionless point may be found. The result being that either longitudinal or torsional motion will be communicated to the handpiece and thereby to the operator holding the handpiece. Although, vibration isolators can be utilized to prevent the communication of such unintended motion, if they are truly isolating they invariably complicate construction of the device and, if simple, consume power in the form of heat generated by contact with a moving surface. Hence, Boukhny's device is both complicated to operate, needing two separate power sources, and is difficult to construct.

Although the magnetostrictive transducers have been replaced by more efficient piezo-electric transducers, the coupling of energy into the torsional mode is much lower than the coupling of energy into the longitudinal mode. Typical measured values of effective coupling coefficient for torsional mode are between 0.04 and 0.08 whereas the effective coupling of longitudinal mode is typically >0.1. FIG. 4 shows a damped torsional mode characteristic (x) compared with the longitudinal mode (y). This results in significantly higher value of electrical impedance that typically has a large reactive component. This can present a system control problem and the high operating voltage limits the torsional mode power that can be delivered to the operative site.

Therefore, as to these L-T transducer systems, Rozenberg in "Sources of High-intensity Ultrasound," Volume 2 concludes that "despite the number of obvious advantages of Longitudinal-Torsional mode (L-T) systems, they have not been put to use on a sufficient scale. One of the main reasons for this is a lack of at least an approximate method for the calculation of such systems" This problem is compounded because the experimental optimization process is complex and involves the fabrication of a large number of sample L-T waveguides.

For reasons stated above, there is a need for optimized ultrasonic transducers that provide torsional modes of motion and/or L-T modes of motion. In particular, there is a need for small, uniaxial, light weight relatively low power torsional and L-T handpieces for medical applications including phacoemulsification applications and dental applications, such as for example, but not limited to, teeth cleaning and tooth extraction. Additionally, there is a need for higher power L-T transducer systems for industrial applications and also medical orthopedic applications such as bone cutting. The invention described herein addresses these and other needs.

SUMMARY OF THE INVENTION

The present invention relates to the design of torsional mode and L-T mode piezoelectric transducer subassemblies and systems primarily intended for medical and dental applications. Similar transducer subassemblies and systems could also be used for industrial applications. The invention provides transducers systems with improved performance and a capability to operate more efficiently in a combined longitudinal-torsional mode of vibration.

One aspect of the invention, provides for piezoelectric transducer subassemblies and systems comprising inhomogeneous resonator sandwiched between two piezoelectric stacks. This aspect of the invention improves on prior art by enabling the size and weight of torsional mode and L-T transducers subassemblies and systems to be reduced. The power handling capability of these transducer subassemblies or systems is also improved over prior art when the stacks are operating in a push-pull mode, as this enhances the torsional motion within the resonator In various embodiments of the invention, an inhomogeneous resonator is coupled to and in-between two piezoelectric stacks. One of the piezoelectric stacks is also coupled to a horn that may optionally include a end-effector, which is designed to couple torsional vibrations or a combination of torsional and longitudinal vibrations to a solid or fluid medium.

The piezoelectric stacks are comprised of piezoelectric elements and optionally end masses. The piezoelectric elements are polarized and electrically connected in parallel. In certain embodiments, one piezoelectric stack in a subassembly or system operates with in-phase synchronism and the second piezoelectric stack operates with phase-opposite synchronism (see e.g., FIG. 6). In other embodiments, both piezoelectric stacks operate with in-phase synchronism.

A horn is coupled to the subassembly system (resonator and piezoelectric stacks). In some embodiments, the horn is attached to the piezoelectric stack. In other embodiments, that horn extends through the center of the piezoelectric stack and is coupled at a nodal region distal from inhomogeneous resonator and proximal to the piezoelectric stack through which the horn is passing.

In a second aspect, the present invention provides for transducer systems that comprise a piezoelectric stack sandwiched between an inhomogeneous resonator and a horn. In yet another aspect of this invention, mountings and methods suitable for mounting a transducer in a stationary structure such as a handpiece housing are provided.

These and other aspects of the invention will be apparent upon reference to the following detailed description and attached figures. To that end, patents, patent applications, and other documents are cited throughout the specification to describe and more specifically set forth various aspects of this invention. Each of these references cited herein is hereby incorporated by reference in its entirety, including the drawings.

BRIEF DESCRIPTION OF THE DRAWINGS

The novel features of the invention are set forth with particularity in the claims. The invention itself, however, both as to organization and methods of operation, together with further objects and advantages thereof, may best be understood by reference to the following description, taken in conjunction with the accompanying drawings described below:

FIG. 14A is a prior art torsional mode transducer system; and FIG. 14B illustrates a transducer system in accordance with embodiments of the present invention;

In the following description of the invention, references are made to the accompanying drawings, which form a part hereof, and in which is shown by way of illustration various embodiments in which the invention may be practiced. It is to be understood that other embodiments may be utilized, and structural and functional changes may be made without departing from the scope of the present invention. It is also to be understood that components and functionality depicted as separate or discrete blocks/elements in the figures may be implemented in combination with other components and functionality, and that the depiction of such components and functionality in individual or integral form is for purposes of clarity of explanation, and not of limitation.

DETAILED DESCRIPTION OF THE INVENTION

A. Terms and Definitions

The following terminology and definitions apply as used in the present application.

The phrase "inhomogeneous resonator" refers to a component, such as for example, but not limitation, a rod, bar, spring, with a non-uniform cross sectional region that generates torsional and longitudinal motion. In some embodiments, an inhomogeneous resonator is a spiral spring or a twisted bar. In other embodiments, a inhomogeneous resonator is a rod with one or more slots.

The phrase "piezoelectric stack" means a two or more piezoelectric elements, such as for example, but not limited to, piezoelectric rings, electrically connected in parallel, which are stacked or held in compression by a bolt or other means. A piezoelectric stack can optionally have an endmass coupled to one or both of the outer piezoelectric elements.

B. Transducer Subassemblies and Systems of the Invention

The present invention is directed to ultrasonic transducer subassemblies and systems designed to operate in torsional modes of vibration or L-T modes of vibrations and, more particularly, to those used for surgical, dental, and industrial welding applications.

Methods and devices employing ultrasonic torsional or L-T mode transducers subassemblies and systems in accordance with the present invention may incorporate one or more of the features, structures, methods, or combinations thereof described herein below. For example, but not limited to, ultrasonic L-T mode transducers can be designed to include one or more of the features and/or processes described below. It is intended that such a device or method need not include all of the features and functions described herein, but may be implemented to include one or more features and functions that, alone or in combination, provide for unique structures and/or functionality.

Figure 6:
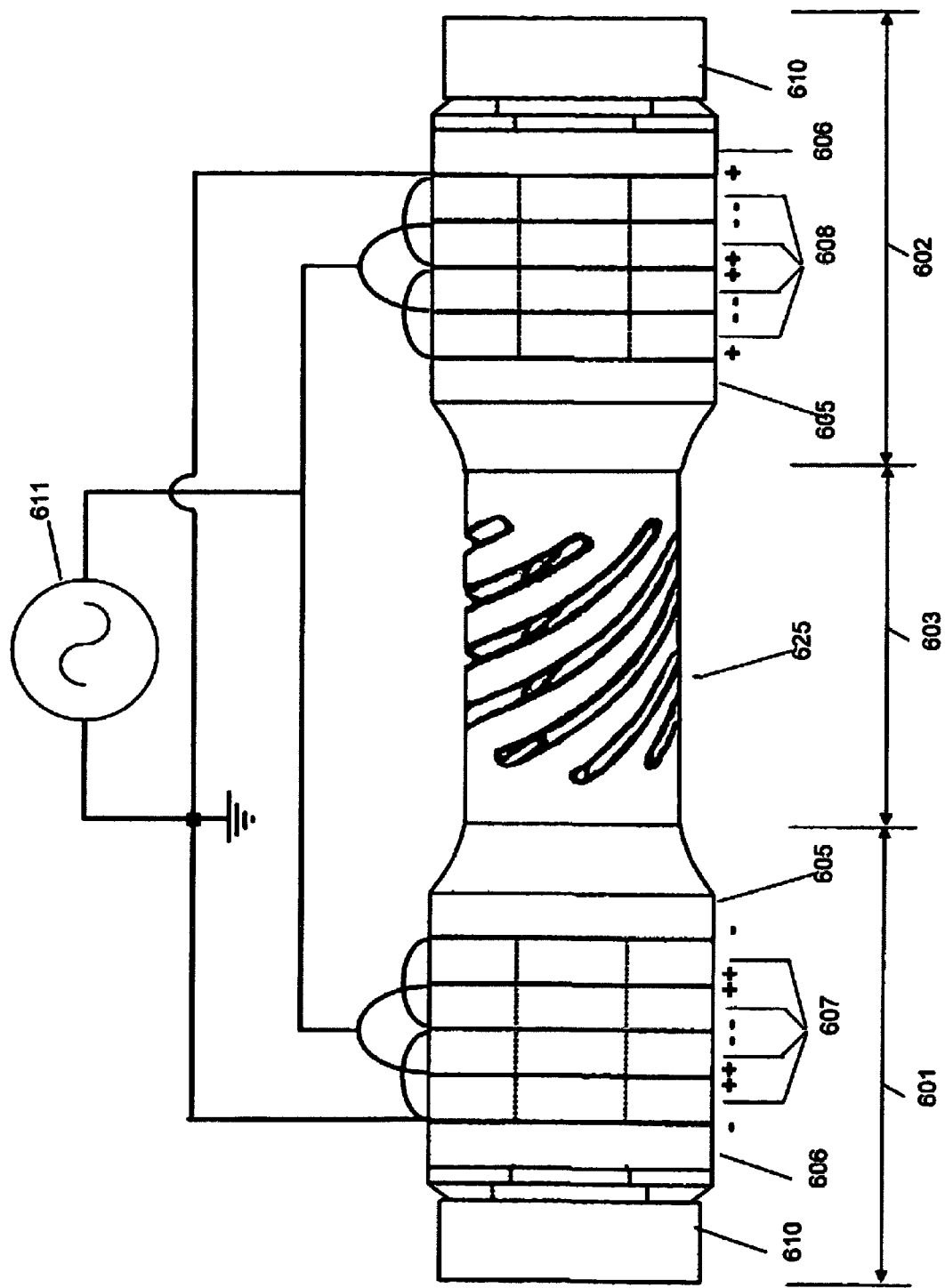
FIG. 6 is a method of electrical connection for a torsional mode transducer system in accordance with embodiments of the present invention.

One aspect of the invention provides piezoelectric transducer subassemblies and systems comprising an inhomogeneous resonator between two piezoelectric stacks, For simplicity the first embodiment is best illustrated by initially considering the mode of operation of a subassembly prior to the attachment of a horn as shown in FIG. 6.

In FIG. 6 piezoelectric stacks 601 and 602 are coupled to a resonator 603 that comprises an inhomogeneous cross section region including one or more slots 625. This inhomogeneous resonator performs a helical spring function by converting longitudinal motion to torsional motion. Any component that allows for this converting longitudinal motion to torsional motion can be used. Some non-limiting examples of inhomogeneous resonators include a spiral spring or a twisted bar. In other embodiments, a inhomogeneous resonator is a rod with one or more slots.

Piezoelectric stack 601 contains piezoelectric elements, e.g., rings 607 that are electrically connected in parallel and have their negative poles at ground potential. There can be any even number of piezoelectric elements 607 that are stacked together and held in compression by bolt 610. Piezoelectric stack 602 contains piezoelectric elements 608 that are electrically connected in parallel and have their positive poles at ground potential. In one preferred embodiment, piezoelectric stack 602 has the same number of piezoelectric elements as piezoelectric stack 601. In other embodiments, piezoelectric stack 602 has a different number of piezoelectric elements than piezoelectric stack 601. Piezoelectric elements 608 are stacked together and held in compression by bolt 610. The components within the subassembly shown are generally of annular cross section. The subassembly is electrically connected to a generator 611. In some embodiments, the metal components within piezoelectric stacks 601 and 602 are at ground potential as shown. In other alternate embodiments, electrical insulators such as alumina oxide ceramic rings (not shown) could be disposed between the distal and proximal ends of the stacks of piezoelectric elements 607 and 608 and end masses 605 and 606. The generator can then be configured to operate in a manner whereby the output is isolated from ground potential. It is also possible that when the generator is isolated from ground potential that piezoelectric stack 601 can be electrically connected with reverse polarity with respect the polarity of piezoelectric stack 602, thereby enabling the poles of the piezoelectric rings within each stack to be the same (i.e.), one piezoelectric stack operates with in-phase synchronism and the second piezoelectric stack operates with phase-opposite synchronism).

Figure 7:
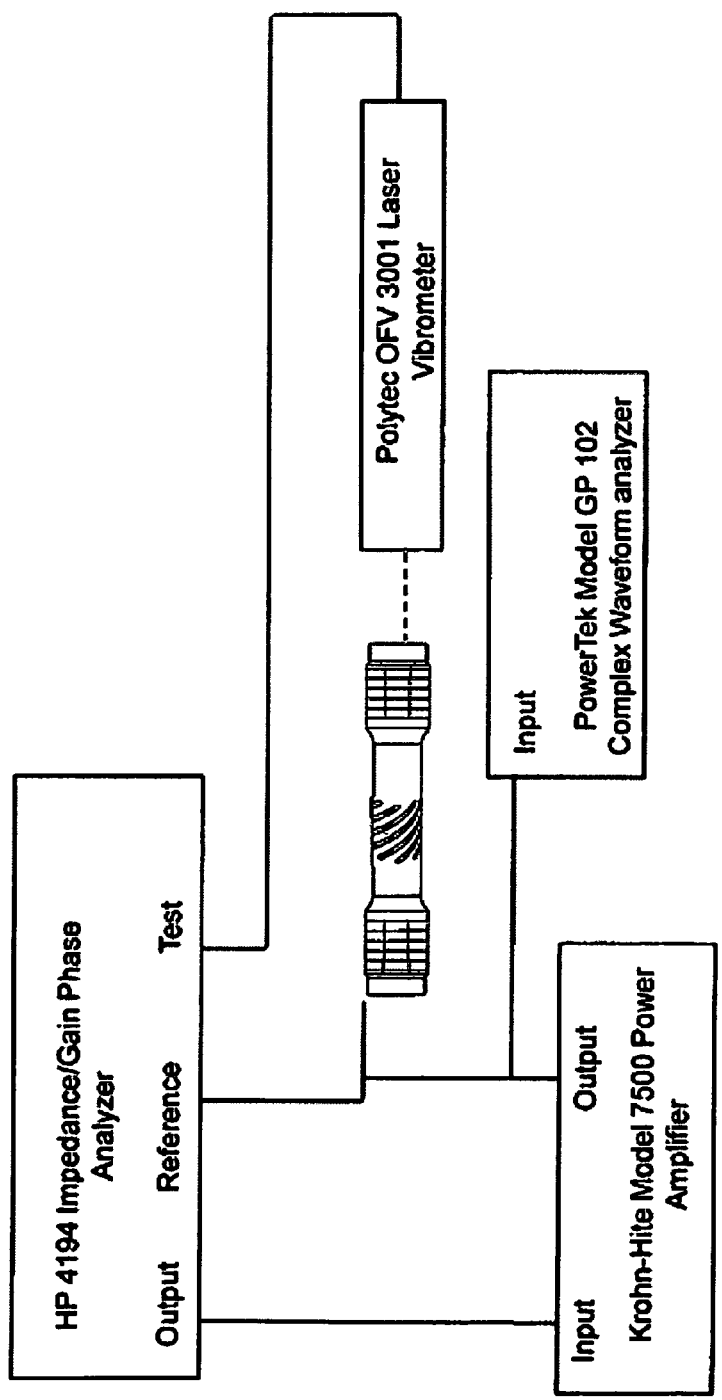
FIG. 7 illustrates a system configured to measure the performance of torsional mode transducers in accordance with embodiments of the present invention.
Figure 8:
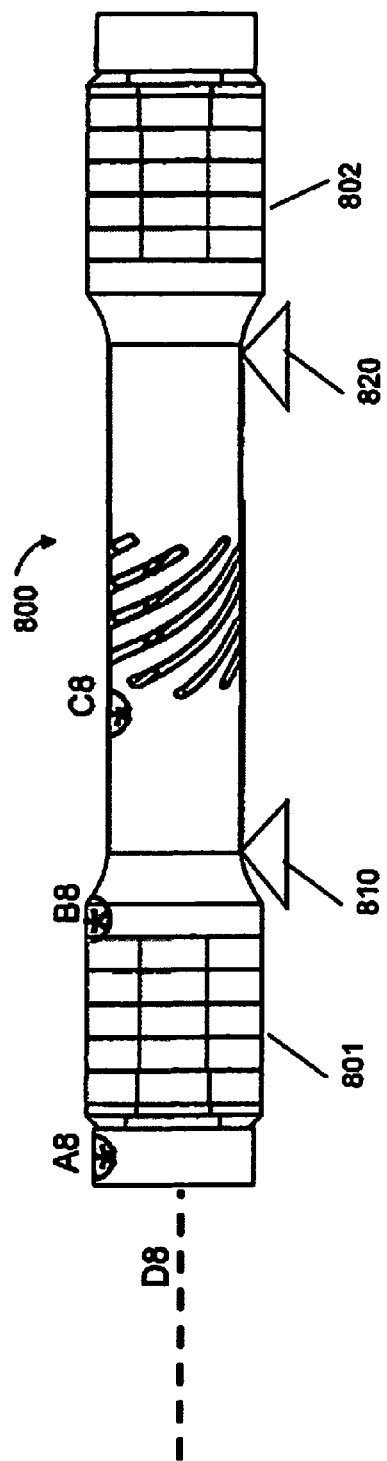
FIG. 8 illustrates a torsional mode transducer system configured for measurement using the measurement system illustrated in FIG. 7 in accordance with embodiments of the present invention.

To determine the optimal configuration, the high power measurement instrumentation shown in FIG. 7 was used. The torsional mode of vibration was measured at points signified by an * in FIG. 8. An end mill was used to machine a reflective surface approximately 1 mm in diameter that is perpendicular to the focused laser beam. The transducer subassembly 800 was compliantly mounted by means of Teflon cradles 810, 820 located at the positions shown. The laser vibrometer was used to measure the velocity at points A8, B8, C8, and D8. For each measurement the power was adjusted to 1 watt and the frequency fine tuned for maximum velocity (at the 29 kHz torsional resonance). The displacements were calculated from the velocity and frequency measurements and the results are tabulated in Table 1.

TABLE 1

| Displacement data | | | |
|---|---|---|---|
| A8 | B8 | C8 | D8 |
| 1.9 µm p-p | 0.36 µm p-p | 5.1 µm p-p | 0.4 µm p-p |

Figure 9:
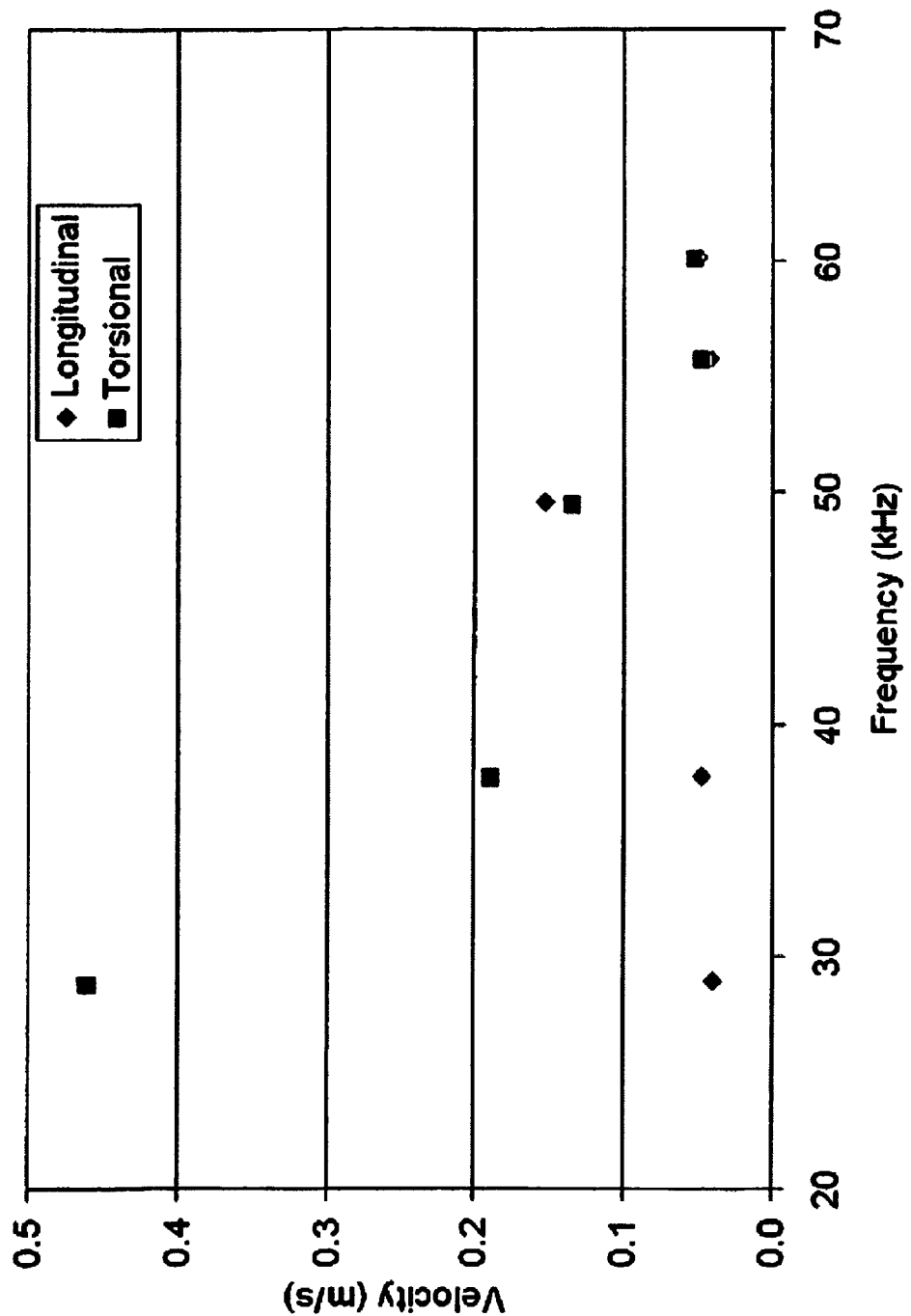
FIG. 9 is a graph of velocity versus frequency for one transducer stack with reverse polarity in accordance with embodiments of the present invention.

The results indicate that point B8 is located very close to a node, defined as a region of minimum displacement. Anti-nodes defined as regions of maximum displacement occur at point A8 and close to point C8. The results also confirm that the longitudinal component of vibration is very small (0.4 µm p-p). With the laser focused at point A, the frequency was swept over the range 5 kHz to 70 kHz in order to search for torsional resonances. The search procedure was repeated for longitudinal resonances with the laser focused at point D8. For each resonance frequency the power was adjusted to 1 watt and the velocity was measured using the laser vibrometer. A map of the relative intensity of the resonant modes is shown in FIG. 9.

Figure 10:
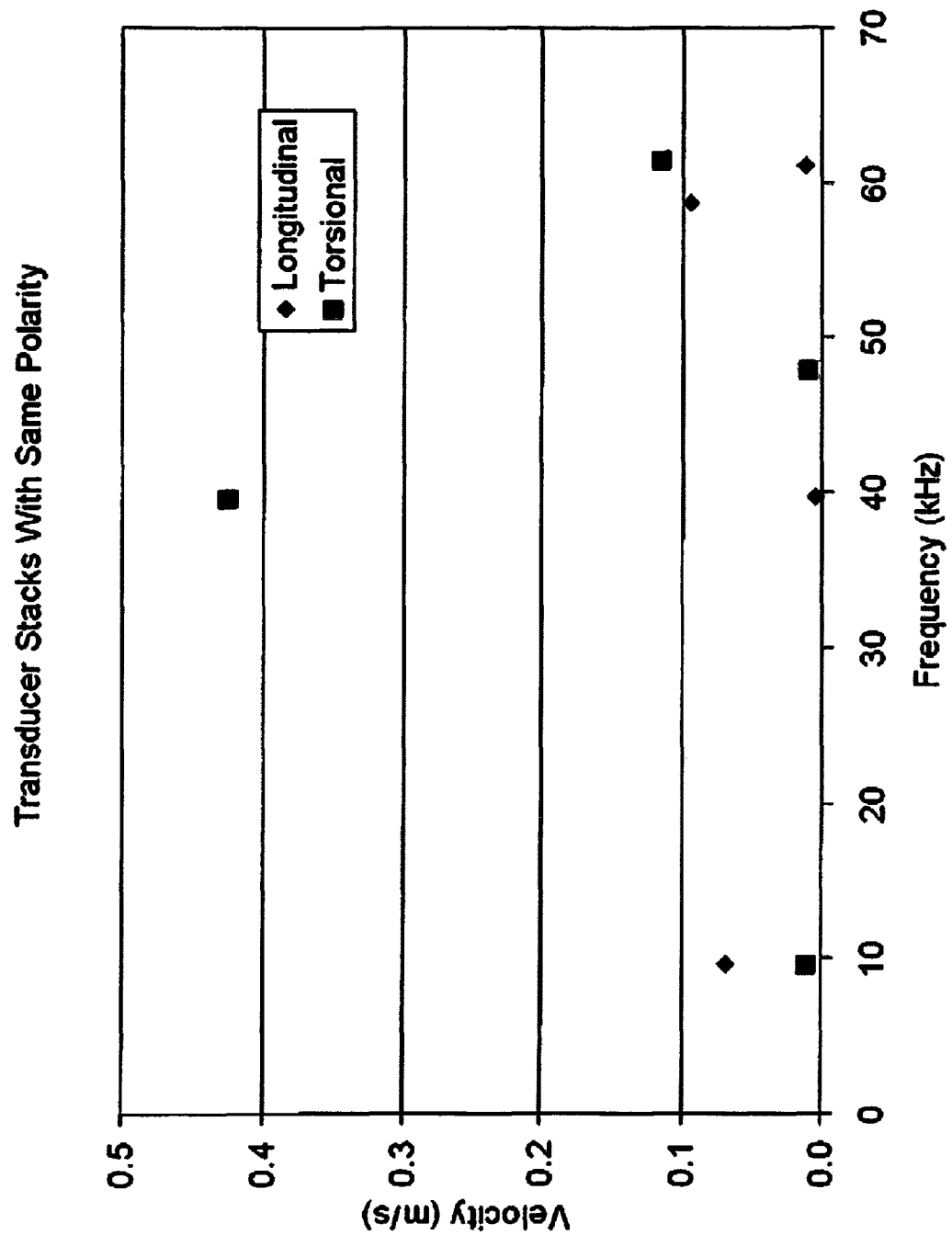
FIG. 10 is a graph of velocity versus frequency for transducer stacks with similar polarity in accordance with embodiments of the present invention.

The transducer system was then reconfigured such that the negative poles of the piezoelectric rings were at ground potential for both piezoelectric stack 801 and piezoelectric stack 802. The resonance search procedure for both torsional and longitudinal modes was repeated and a map of the relative intensity of the resonant modes is shown in FIG. 10.

An analysis of the experimental data indicates that configuring piezoelectric stack 801 and piezoelectric stack 802 so that both piezoelectric stacks operate with in-phase synchronism suppresses the level longitudinal vibration over the frequency range of 5 kHz to 70 kHz. A relatively strong torsional mode was detected at 39.6 kHz. Configuring piezoelectric stack 801 and piezoelectric stack 802 such that one piezoelectric stack operates with in-phase synchronism and the second piezoelectric stack operates with phase-opposite synchronism (i.e., with reverse polarity) is the preferred embodiment because it has the most efficient torsional mode at the lowest frequency (29 kHz). It can also be operated in a combined L-T mode at 50 kHz.

Figure 11:
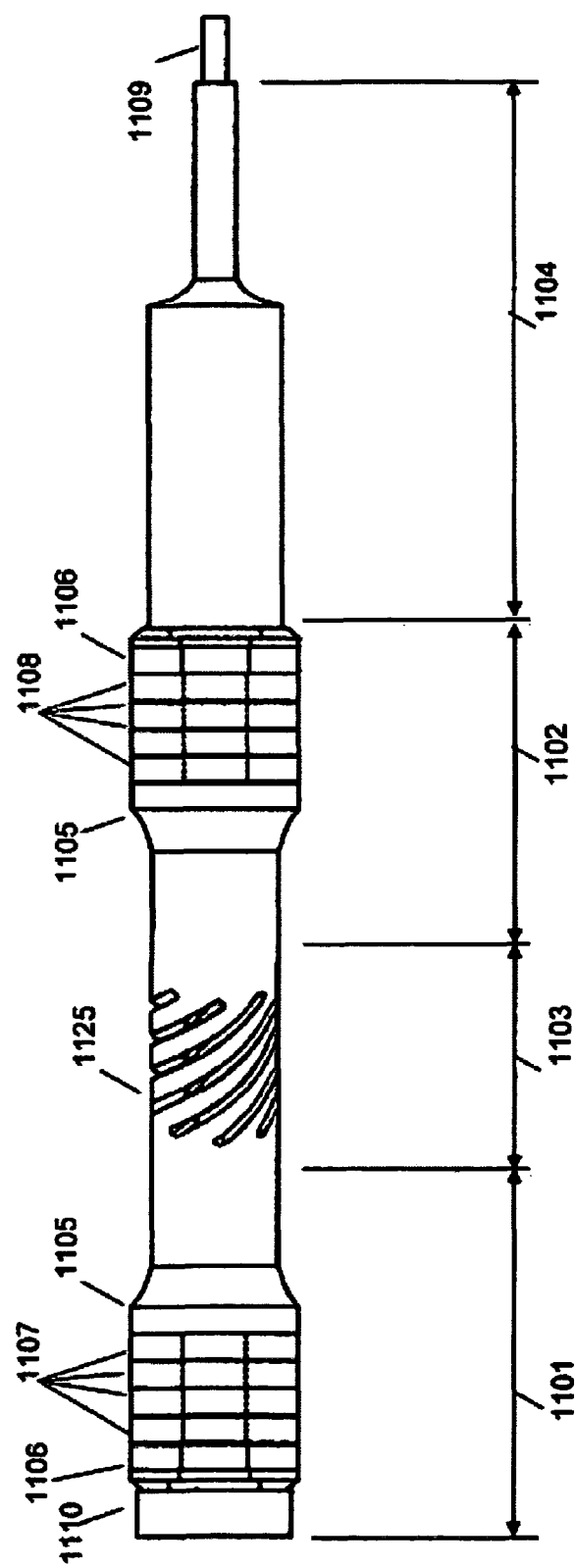
FIG. 11 is a torsional mode transducer system in accordance with embodiments of the present invention.

The subassembly's relatively low measured torsional and longitudinal displacements can be amplified by attaching a horn as illustrated in FIG. 11. The bias bolt for piezoelectric stack 1102 can be an integral part of horn 1104 and is coupled (for example, but not limited to threadingly engaged) to end mass 1105. Horn 1104 is proximally coupled to piezoelectric stack 1102. The horn is typically designed such that a cross section of the horn distal to the piezoelectric stack is smaller than a cross section proximal to the piezoelectric stack. The components within the assembly shown are generally of annular cross section with the exception of the end effector 1109.

Figure 12:
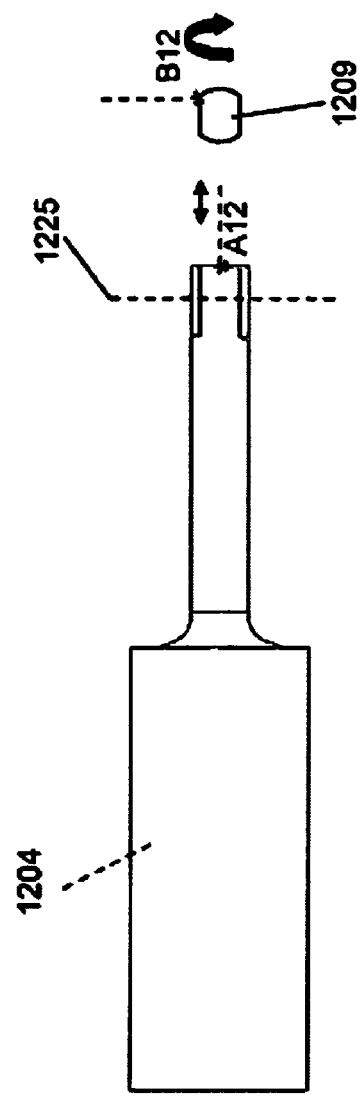
FIG. 12 is a distal horn portion of the torsional mode transducer system illustrated in FIG. 11.
Figure 13:
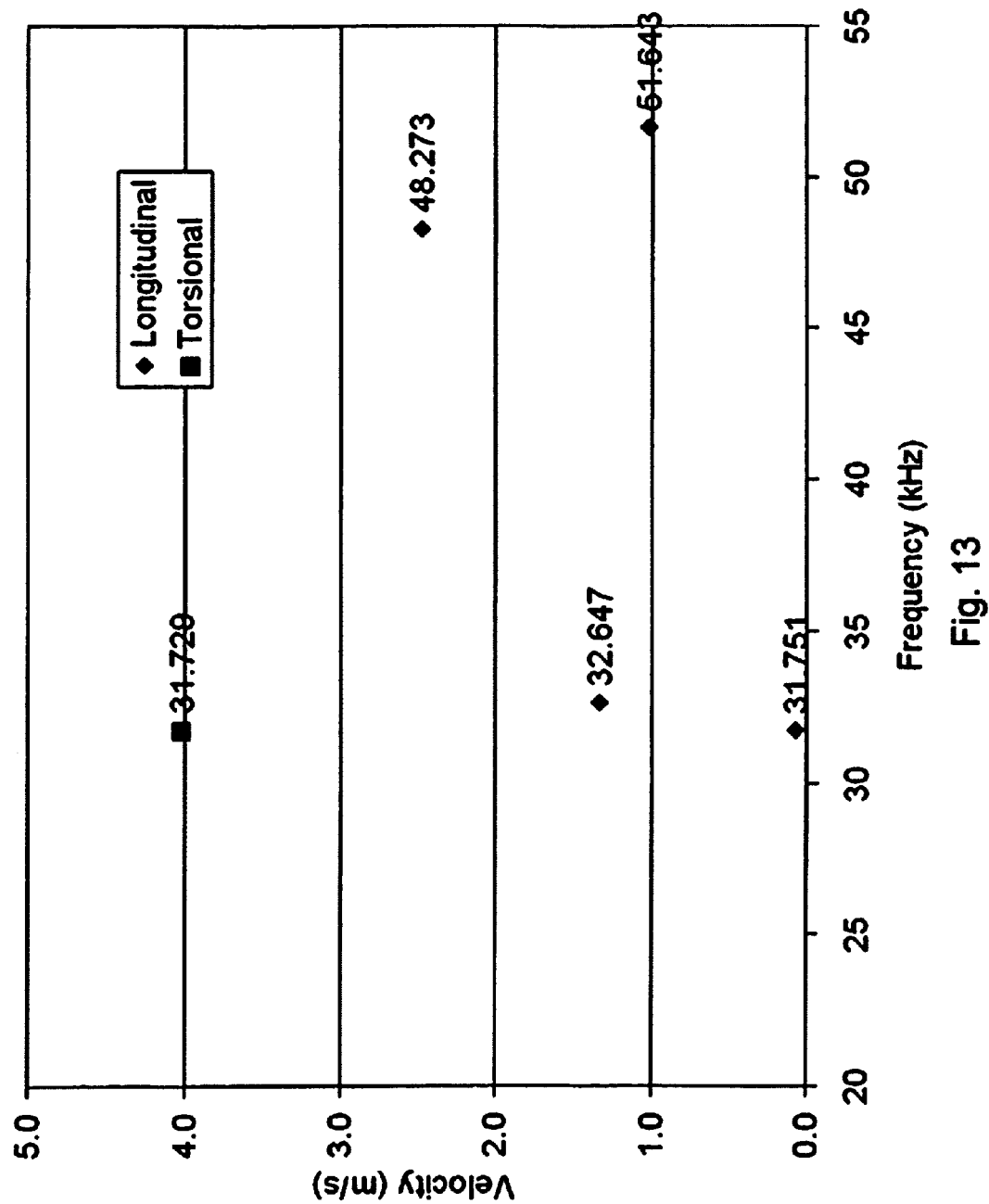
FIG. 13 is a graph of velocity versus frequency for the torsional mode transducer system illustrated in FIG. 11.

For purposes of an illustrative example, flats were formed in order to facilitate the measurement of torsional velocity as shown in FIG. 12. The flats also help demonstrate functionality by coupling torsional mode energy into a fluid medium such as water. A laser vibrometer was used to measure both the longitudinal and torsional vibrations of the distal horn region 1209. The laser beam at point A12 was aligned with the longitudinal motion of the distal tip of the horn 1204. The laser beam at point B12 was perpendicular to the machined flats at the distal tip 1209 of the horn, illustrated in cross-section 1225. The beam was adjusted such that it is focused off the axis rotation in order to measure the maximum torsional vibration. The high power performance of the transducer system shown in FIG. 11 was measured using the instrumentation shown in FIG. 7. The input power was held constant at 1 watt and the frequency fine tuned for the maximum velocity measured by the laser vibrometer. A velocity map of the torsional and longitudinal resonant modes is shown in FIG. 13.

The same measurement method was used for a more detailed analysis of the torsional mode at 31.7 kHz. In all cases, the frequency was in the range 31.7 kHz±0.1 kHz. The transducer system shown in FIG. 11 was electrically connected to the power source in 3 different configurations. Initially, just piezoelectric stack 1101 was driven with piezoelectric stack 1102 not connected and left in an open circuit condition. Following this, piezoelectric stack 1102 was driven with piezoelectric stack 1101 not connected and left in an open circuit condition. Finally, both piezoelectric stacks were connected as shown in FIG. 11 (with one piezoelectric stack operating with in-phase synchronism and the second piezoelectric stack operating with phase-opposite synchronism; i.e., with piezoelectric stack 1101 having a reverse polarity with respect to piezoelectric stack 1102). The measured data is tabulated below in Table 2.

TABLE 2

| Multiple transducer tabulated data. | | | | |
|---|---|---|---|---|
| System | L Mode A µm p-p | T Mode B µm p-p | Volts r.m.s | Z Ω | Phase degrees |
| 1101 only | 2.1 | 52.2 | 106 | 1760 | −82 |
| 1102 only | 2.7 | 53 | 44 | 1396 | −52 |
| 1101 + 1102 | 1.7 | 64.2 | 33 | 611 | −47 |

Figure 1:
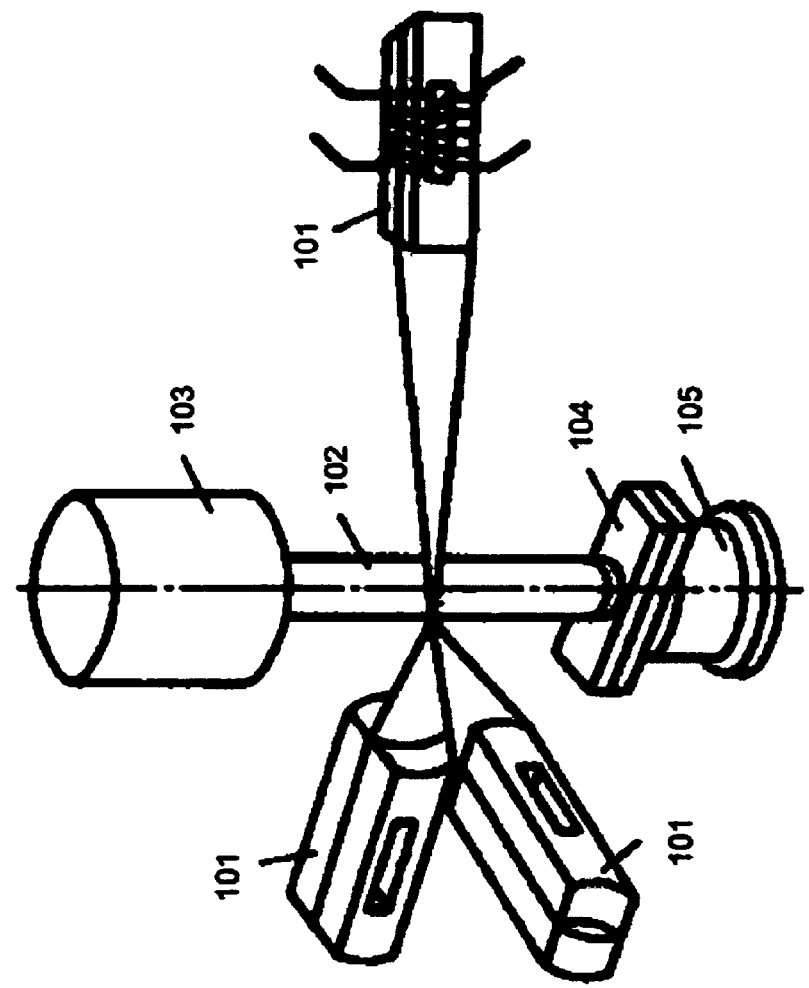
FIG. 1 is an illustration of a prior art industrial torsional welding system.
Figure 2:
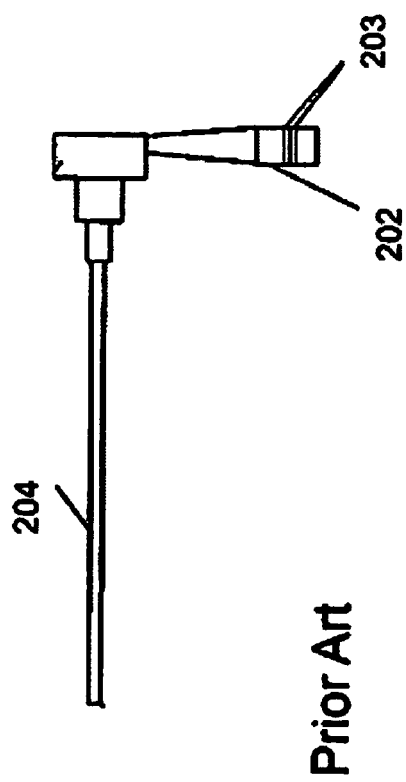
FIG. 2 is an illustration of a prior art transducer assembly that converts longitudinal motion to torsional motion.
Figure 3:
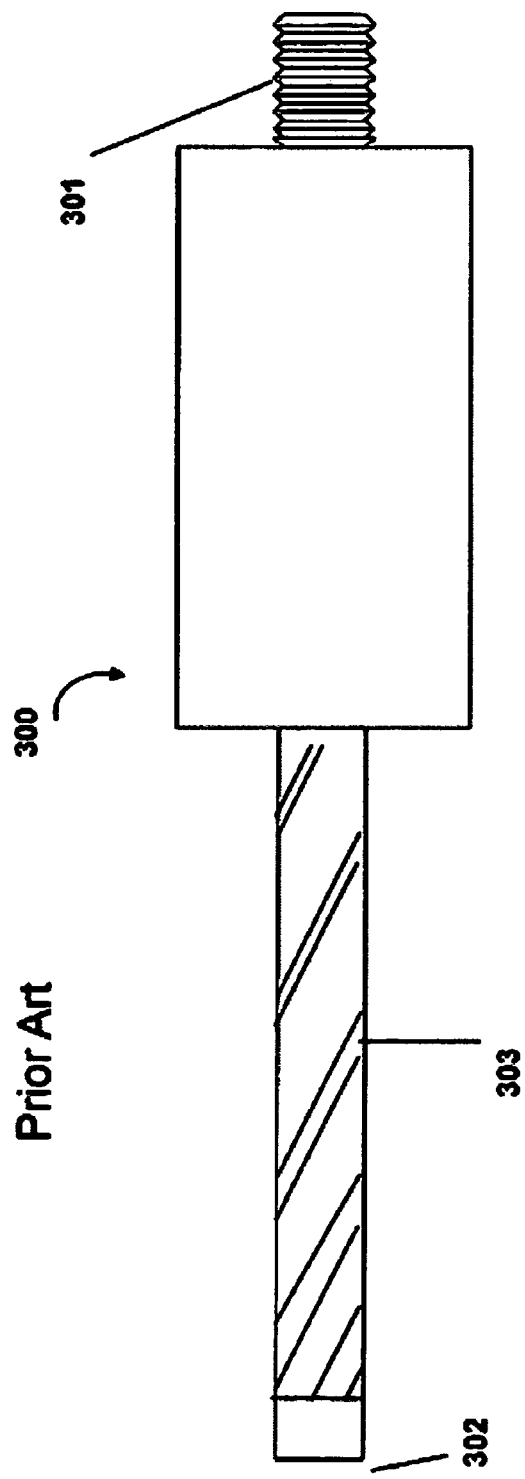
FIG. 3 is an illustration of a prior art L-T horn.
Figure 4:
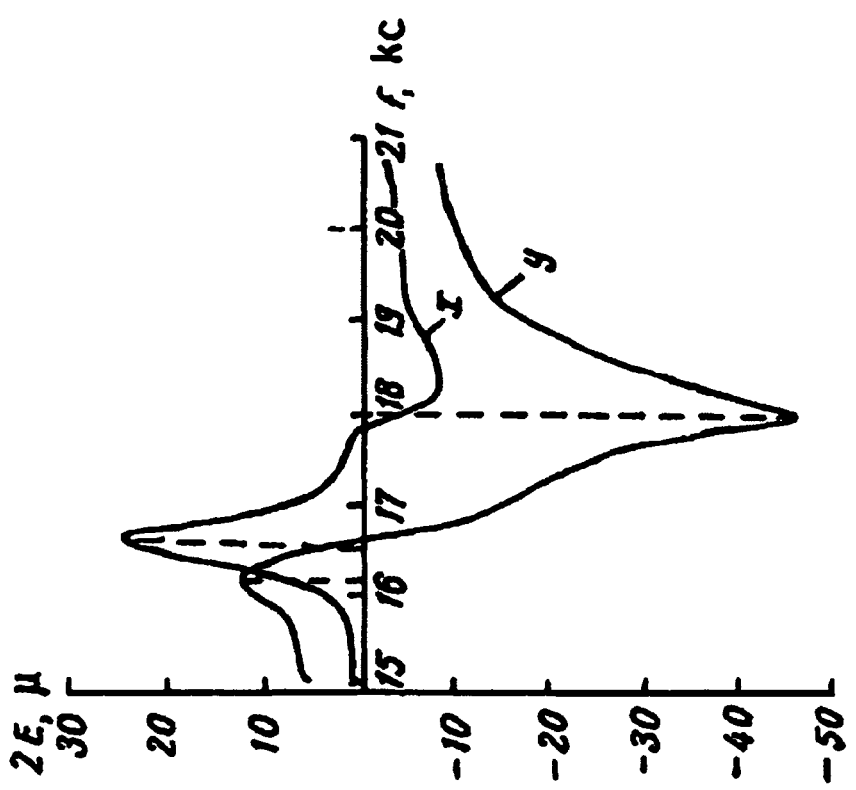
FIG. 4 is a graph illustrating the variation of L-T vibrations at the distal tip of a prior art horn as a function of frequency.
Figure 5:
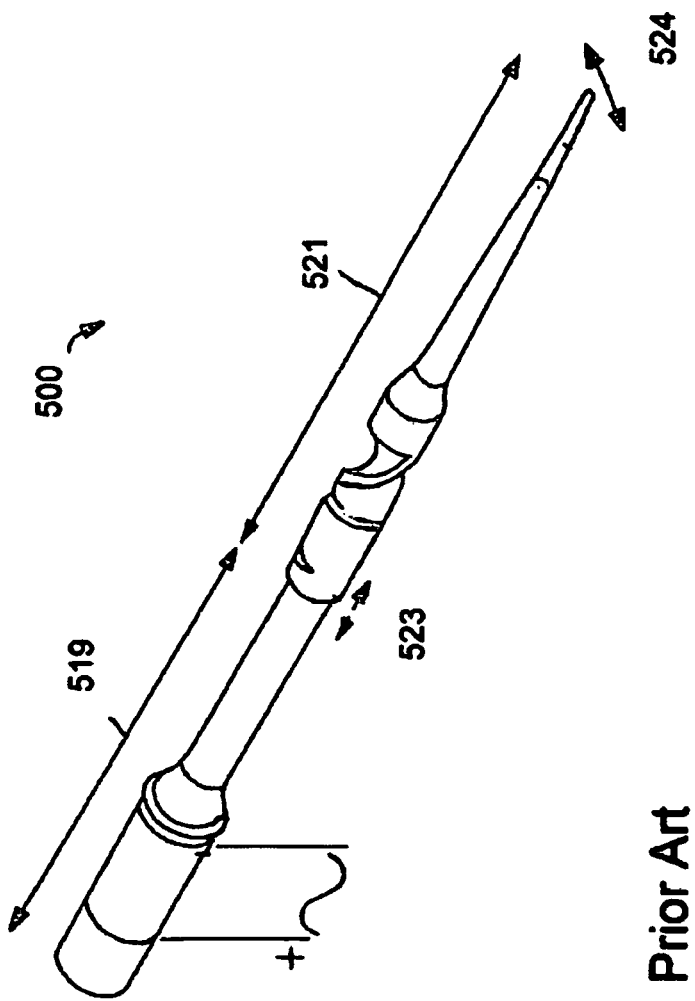
FIG. 5 is an illustration of a prior art L-T medical transducer for biological tissue dissection.

The system with only piezoelectric stack 1101 is representative of the geometry used in prior art transducers, such as those illustrated by Wuchinich in FIG. 5. The distal piezoelectric elements 1108 become passive components that form part of a modified resonator section. One aspect of this invention is based on the measured performance improvement when a resonator is sandwiched between two separate piezoelectric stacks (System 1101+1102) in table 2. For this configuration, the drive voltage was reduced as a result of lower impedance and a more favorable phase angle between the voltage and current. Reducing the drive voltage to an absolute minimum improves patient safety for medical applications and improves reliability by reducing the risk of voltage breakdown.

Figure 15:
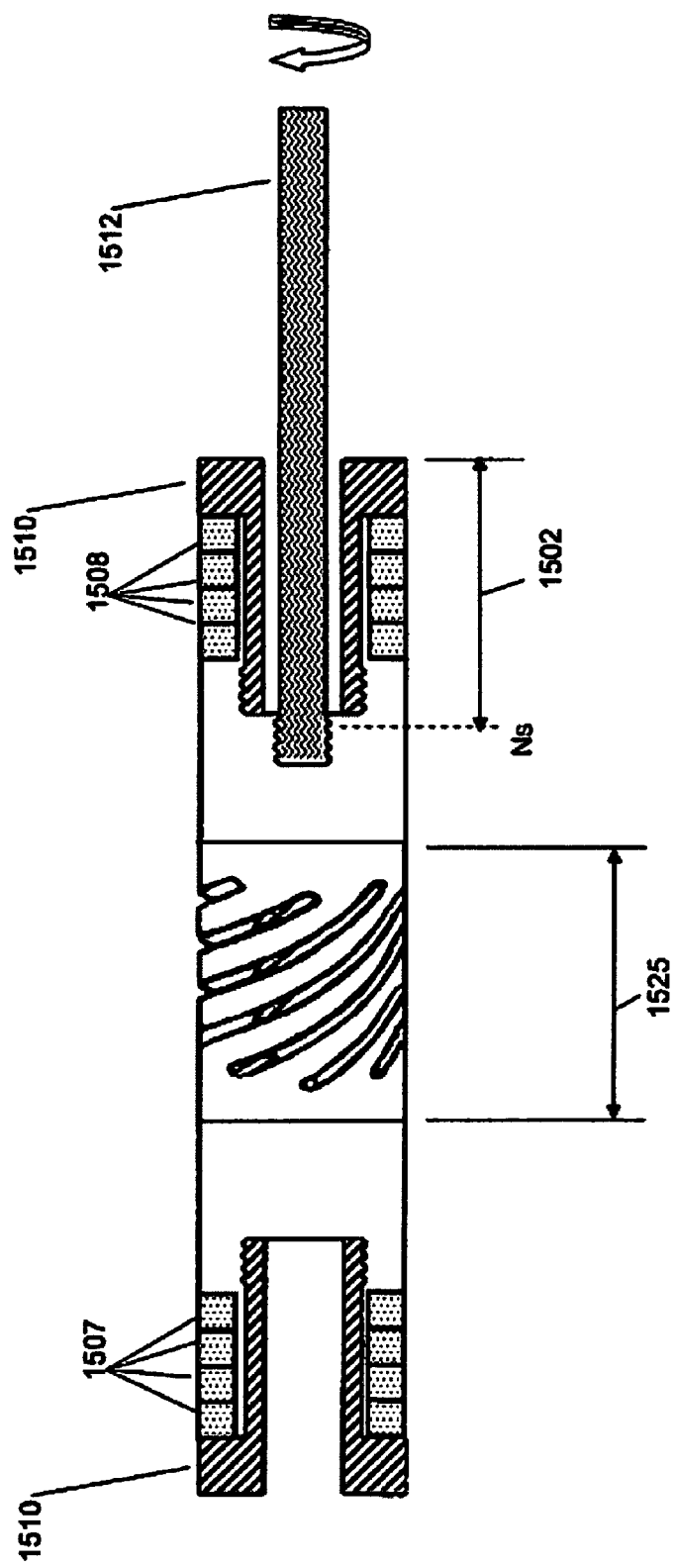
FIG. 15 is a cross-sectional view of a torsional mode transducer in accordance with embodiments of the present invention.

In yet further embodiments of this aspect of the invention, the horn is attached at a nodal position on torsional mode transducer systems. In U.S. Pat. No. 3,681,627, Murry et al describes a method whereby the shaft of an operative tool is attached at a nodal position and reverses direction such that it passes back through the center of the transducer. The Murry patent is limited, however, only to longitudinal modes of vibration. The present invention provides for configurations that are applicable for use with torsional mode transducers. The measured data relating to FIG. 11 indicates the presence of a shear mode displacement node in the region distal to the inhomogeneous resonator section 1103 and proximal to piezoelectric stack 1102. Referring now to FIG. 15; by anchoring a reverse direction torsional mode horn at the nodal location Ns, the overall length of the transducer assembly can be reduced as shown. In FIG. 15, the piezoelectric elements 1507 are stacked together and held in compression by bolt 1510. The bolt 1510 differs in the design illustrated in FIG. 11 in that it has an annular hollow cross section. Also, for this embodiment the piezoelectric elements 1507 and 1508 have a relatively large internal diameter such that horn 1512 can pass through the center of piezoelectric stack 1502. Horn 1512 is attached at a torsional (shear wave) nodal location defined in FIG. 15 as Ns. The horn can be attached to the body of the transducer system by means known to those skilled in the art. Examples include, by are not limited to, a threading engagement of the horn 1512 or by dimensioning the diameter of the horn 1512 and the hole in the transducer system to achieve an interference press fit. The length of the horn is typically one quarter wavelength with the physical length being related to the shear mode velocity and the frequency of operation. Any number of additional half wavelength sections can be added to the length of the horn.

A second aspect of this invention provides for piezoelectric transducer subassemblies and systems comprising an inhomogeneous resonator coupled proximal to a single piezoelectric stack. This design is based on the measured performance improvement when the torsional mode resonator is coupled proximal to a single piezoelectric stack (1102 only in table 2).

By means of an illustrative example of the second aspect of this invention, an improved phacoemulsification transducer system design is compared with a prior art design geometry which is illustrated in FIG. 14A. This prior art transducer system design geometry has a longitudinal resonant frequency corresponding with an accumulated component length of one and a half wavelengths (1.5λ). A central annular aspiration lumen extends along the entire length of the assembly and extends proximally as a tube 1401 and distally through a hollow needle 1406. The rear mass 1402 is attached to piezoelectric rings that are stacked together and pre-compressed by a bolt section (not shown) that is an integral part of the rear mass 1402 and is threadingly engaged in front mass 1407. When connected to an electrical generator, the piezoelectric ceramic stack provides the motive force and couples mechanical vibrations to front mass 1407. Front mass 1407 is mechanically attached to an inhomogeneous resonator section 1403. The resonator has one or more slots, which performs a helical spring function and converts longitudinal motion to torsional motion. The resonator section 1403 is mechanically coupled to a velocity amplifying horn 1405. Solid horns are sometimes referred to as concentrators, rods, tools, and amplitude or velocity transformers. The horn illustrated has a stepped geometry with transitional radius but other geometries such as conical and exponential could be used. The distal tip of hollow needle is the end effector 1406 and is threadingly engaged in horn 1405. For torsional out of plane motion, the distal end of the needle is bent such that torsional motion within the needle shaft is translated into transverse motion at the operative tip.

The second aspect of this invention is illustrated in FIG. 14B. The design geometry has been changed from the prior art design discussed above, in that the transducer system has a longitudinal resonant frequency corresponding with a half wavelength (λ/2). The location of the inhomogeneous resonator 1403 has been changed such that it is coupled proximal to the piezoelectric stack 1404. The rear mass 1407 in the prior art transducer has been eliminated. In this illustrative example of the invention, all the metal components were fabricated from 6Al-4V titanium alloy and the piezoelectric elements 1414 were fabricated from a generic Navy Type III material. Alternative materials for component manufacture include aluminum alloy for horn 1405. Alternate materials for the inhomogeneous resonator 1403 and end mass 1402 include aluminum alloy, stainless steel and beryllium copper. The inhomogeneous resonator could also be fabricated from fiberglass composite. Alternative piezoelectric materials include those that conform to US Navy Type I specifications and also lead free materials such as barium titanate. The four piezoelectric elements that are illustrated in the piezoelectric stack 1404 are electrically connected in parallel and have an outside diameter of 12 mm an inside diameter of 5 mm and a thickness of 2 mm. For medical handpiece applications the outside diameter of the piezoelectric elements can be in the range 6 mm to 35 mm, the inside diameter can be in the range 3 mm to 25 mm, and the thickness in the range 1 mm to 5 mm. The end effector 1406 (e.g., a bent hollow titanium needle) is available from Micro Surgical Technologies. Referring to FIG. 14B, the lengths of the component parts are as follows: 1401 6 mm; 1402 5 mm; 1403 17 mm; 1405 29 mm. The major diameter of horn 1405 is 12 mm at a cross-section 1405A and the minor diameter is 3.8 mm at a cross-section 1405B, for example. The inhomogeneous resonator 1403 has an outside diameter of 12 mm, and a total length of 17 mm. 8 slots on the resonator have a width of 1 mm, a depth of 3.5 mm and a pitch of 34 mm. A cross-section 1403A is illustrated having lines of symmetry 14031 and 14032. A cross section 1403B is illustrated having lines of symmetry 14033 and 14034. Note that lines of symmetry 14031 and 14032 do not align with lines of symmetry 14033 and 14034, e.g there is a rotational asymmetry of the cross-section of the inhomogeneous resonator 1403 along the length of the inhomogeneous resonator 1403. As will be apparent to one of skill in the art various pitches, and widths of slots can be used. Mitskevich (cited above) concludes that the degree of transformation of longitudinal into torsional vibration depends on the depth of the helical grooves and their pitch and increases within defined limits as the depth of the grooves is increased and their pitch is decreased.

The transducer design illustrated in FIG. 14B was tested using the instrumentation illustrated in FIG. 7. The laser was focused side on to the tip of the needle 1406 and the frequency adjusted for maximum displacement. A pure torsional mode could only be sustained up to a maximum value of 21 μm p-p at a frequency of 32.644 kHz. The test results are summarized in table 3.

TABLE 3

Test Data

| Mode | Tip stroke μm p-p | Frequency kHz | Power watts | Voltage Volt r.m.s. | Phase Angle ° |
|---|---|---|---|---|---|
| Torsional | 21 | 32.644 | 0.265 | 40.5 | −52 |
| Longitudinal | 13 | 38.127 | 1.1 | 31.6 | 2 |

The above test data relates to measurements made with the transducer operating in air. Under operational conditions water would be continuously aspirated through the central lumen and this would increase the impedance and drive voltage. The aspiration water also cools the piezoelectric rings and allows operation at power levels up to a maximum of about 30 watts. As can be seen the design has been optimized for torsional mode rather than longitudinal mode of operation.

In another aspect of this invention, a means of mechanically decoupling the torsional and longitudinal vibrations within the transducer assembly from the housing is disclosed. In U.S. Pat. No. 6,984,220 B2, Wuchinich gives a detailed description of the problem but concludes that possible simple solutions would be ineffective. For medical ultrasonic handpieces mechanical coupling of either longitudinal or torsional motion will cause localized heat and the generation of audible sub-harmonic frequencies. The fundamental design problem is associated with the difference in the longitudinal speed of sound $C_L$ in a cylindrical or rectangular bar shaped component compared with the shear mode speed of sound $C_S$. For example, titanium alloy 6Al-4V has a longitudinal speed of sound $C_L \approx 4916$ m/s and a shear mode speed of sound $C_S \approx 3100$ m/s. For the piezoelectric material PZT4 the stiffened shear wave propagation is $\approx 2630$ m/s and the longitudinal wave propagation is $\approx 2900$ m/s. The wavelength ($\lambda$) □ frequency (F) and speed of sound (C) by the formula:

$$C = \lambda/F$$

For example, the longitudinal resonance of a 12 mm diameter titanium alloy bar occurs when the length of the bar equals one half wavelength ($\lambda/2$). For a bar that is 100 mm in length the longitudinal resonant frequency will be 24.58 kHz and the torsional mode resonance frequency will be 15.5 kHz. However, as can be seen in FIG. 14, practical transducers contain components that have complex shapes such as the inhomogeneous resonator 1403, horn 1405 and end effector 1406.

Figure 16A:
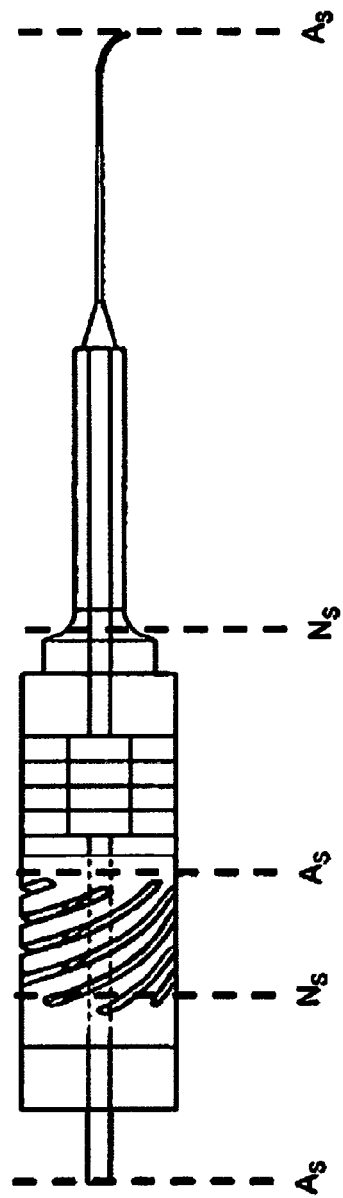
FIG. 16A illustrates the location of torsional mode nodes and antinodes for a transducer system in accordance with embodiments of the present invention.
Figure 16B:
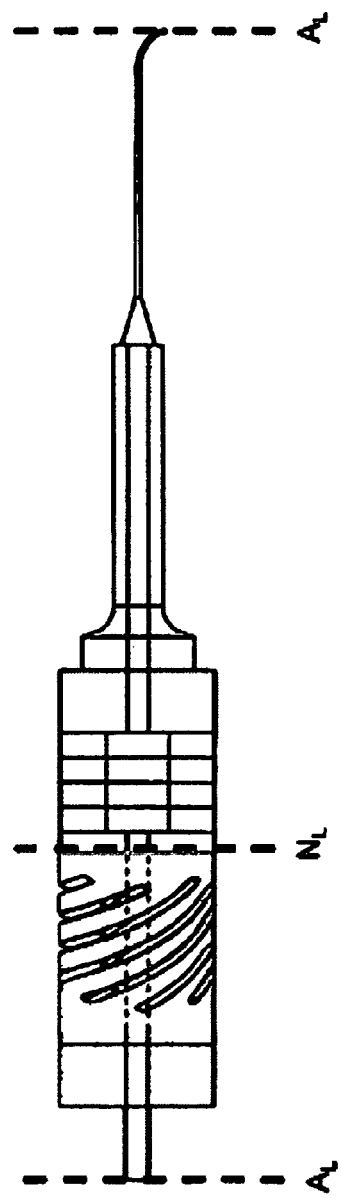
FIG. 16B illustrates the location of longitudinal mode nodes and antinodes for a transducer system in accordance with embodiments of the present invention.

The mode of vibration of the resonator 1403 can be determined using finite element analysis or by practical measurements using a laser vibrometer. FIG. 16A illustrates the position of the nodes ($N_S$) and antinodes ($A_S$) at the torsional mode resonance frequency of 32.644 kHz. A node is defined as a point of minimum torsional displacement and is ideally positioned close to the step in the horn. FIG. 16B illustrates the position of the node ($N_L$) and antinodes ($A_L$) at the longitudinal mode resonance frequency of 38.127 kHz. As can be seen the torsional mode node and longitudinal mode node are spatially separated.

Thus a design optimized for torsional mode would have the housing attached close to the node at the step of the horn. However, while operating at the longitudinal resonance frequency, there will be significant motion at the horn step and this will result in energy being coupled into the housing. Within a transducer system, the coupling of torsional energy ($k_{eff}$) from the relatively small longitudinal motion within the piezoelectric stack is typically within the range 0.02 to 0.08. For unity gain longitudinal transducer systems without a horn attached, i.e., subassemblies, the effective coupling coefficient ($k_{eff}$) is typically within the range 0.2 to 0.4. As low values of $k_{eff}$ result in higher impedance and drive voltage, it is therefore, more important to optimize the decoupling mechanism for torsional rather than longitudinal motion.

Figure 17A:
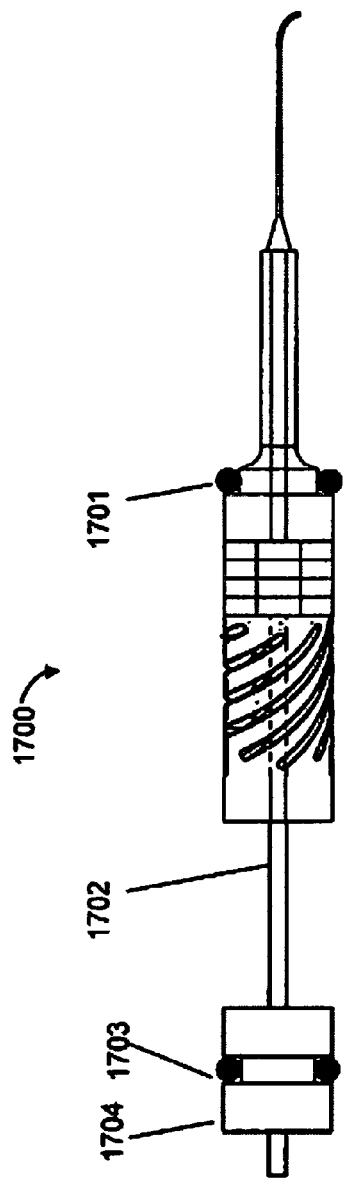
FIG. 17A illustrates a prior art method of positioning the transducer system within a cylindrical housing.

A typical method used to decouple energy within an ultrasonic handpiece designed for phacoemulsification is illustrated in FIG. 17A. The transducer system 1700 is located within a cylindrical housing (not shown). The inside diameter of the housing is dimensioned such that the 'O' ring seals 1701 and 1703 are compressed but still provide an air gap between the internal components and the housing. Typical 'O' ring materials include Nitrile, Neoprene, Butyl, Silicone, Ethylene Propylene (EPDM), and Polytetrafluoroethylene (PTFE). The housing is permanently attached to the heel mass 1704 by either bonding adhesive, brazing, or laser welding. Typically a silicone rubber adhesive such as Dow Corning 577 is used. Additional mechanical decoupling of both torsional and longitudinal motion is achieved by attaching the heel mass 1704 to the transducer assembly by means of a very thin walled small diameter tube 1702. Typically this tube would be fabricated from titanium alloy or stainless steel, have a length between 10 mm and 20 mm, an outside diameter between 2.5 mm and 3.5 mm and the thinnest possible wall thickness (between 0.3 mm and 0.5 mm). The combination of this very compliant tube 1702 and the relatively large heel mass 1704 provide decoupling for both torsional and longitudinal motion that is generated within the transducer assembly. The problem is associated with the distal mounting location at the step of the horn in that 'O' ring 1701 will tend to convert motional energy into heat and will not anchor or adequately center the transducer assembly within the housing.

Figure 17B:
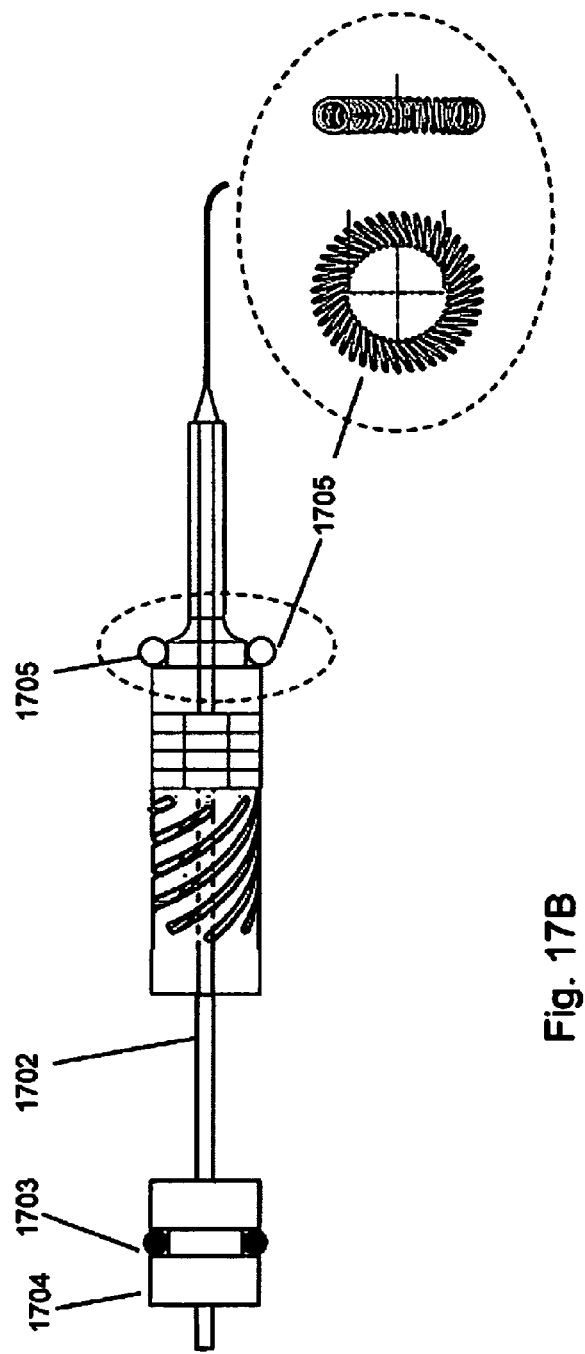
FIG. 17B illustrates a transducer system in accordance with embodiments of the present invention, wherein the vibrations between the transducer system and a cylindrical housing are decoupled.

In this aspect of the invention, a means is provided that properly anchors the assembly within the housing while maintaining electrical continuity between components. One embodiment of the means used is a spring. In some embodiments, the spring is a metal coil spring. In more preferred embodiments, the spring is a canted coil Spring™ manufactured by Bal Seal Engineering Inc. This spring is illustrated in FIG. 17B as component 1705. The spring is designed to perform a latching and holding function that centrally locates annular shaped components within the bore of a housing and to maintain electrical continuity between components. Preferable grooves are placed in a surface region of the transducer system for mounting or holding the transducer system in the housing and the spring is frictionally engaged between the groove on the transducer system and the housing.

The prototype transducer used to evaluate the performance of this aspect of this invention was initially tested with a prior art 'O' 1701 and then modified to substitute a Bal Seal 1705 with the following specification: Spring ID 2.9 mm; Coil Width (ref) 2.3 mm; Coil Height (ref) 2.0 mm; Wire Diameter 0.4 mm; Deflection 1.4 mm; Material Type

TABLE 4

Longitudinal Mode Test Data Measurements

| | Resonant Frequency (kHz) | Mechanical Q Factor | Real Impedance Ohms | Coupling Coefficient |
|---|---|---|---|---|
| 'O'Ring | 34.766 | 280 | 548 | 0.116 |
| Bal Seal | 34.773 | 415 | 353 | 0.117 |

316 Stainless steel. A cylindrical housing was slid over the transducer assembly thereby compressing the Bal seal and clamping the transducer assembly within the housing. The tabulated data in Table 4 is the longitudinal mode low power Impedance Analyzer.

The tabulated data in Table 5 is the torsional mode low power Impedance Analyzer measurements.

TABLE 5

Torsional Mode Test Data

| | Resonant Frequency (kHz) | Mechanical Q Factor | Real Impedance Ohms | Coupling Coefficient |
|---|---|---|---|---|
| 'O'Ring | 33.682 | 317 | 870 | 0.09 |
| Bal Seal | 33.473 | 464 | 843 | 0.074 |

The Table 4 test data indicates that the Bal Seal has very low losses compared with the 'O' ring at the longitudinal mode resonance frequency. As can be seen in FIG. 16B, the longitudinal node $N_L$ is spatially separated from the Bal Seal or 'O' ring located at the step in the horn. Under typical operational conditions, the stroke at the distal tip of the end effector would be approximately 50 μmp-p resulting in a computed longitudinal displacement at the step in the horn of 10 μmp-p. The table 5 torsional mode test data has a smaller variation in mechanical Q and real impedance because the Bal seal and 'O' Ring are located very close to the node at the step of the horn as illustrated in FIG. 16A.

In this aspect of the invention, any seal that is functionally similar can be used, including but not limited to springs encapsulated in a polymer or plastic material. For example, Bal Seal Engineering Inc. manufactures a range of seals that incorporate the canted metal coil springs and Parker Seals also manufacture a PTFE FlexiSeals™ that incorporates a metal coil spring. In the certain embodiments, of this invention the Bal Seal can be located at a torsional shear wave node at the step of a horn. Alternatively, it could also be located within any metal component within the transducer subassembly. A Bal Seal could also be used to replace 'O' ring 1703 that is located in heel mass 1704.

One skilled in the art would readily appreciate that the present invention is well adapted to carry out the objects and obtain the ends and advantages mentioned, as well as those inherent therein. The methods and compositions described herein, as presently representative of preferred embodiments, are exemplary and are not intended as limitations on the scope of the invention. Changes therein and other uses will occur to those skilled in the art, which are encompassed within the spirit of the invention, are defined by the scope of the claims

What is claimed is:

1. A piezoelectric transducer system comprising:
a piezoelectric stack, wherein the piezoelectric stack comprises two or more piezoelectric elements;
an inhomogeneous resonator coupled to the piezoelectric stack, wherein the inhomogeneous resonator comprises a twisted bar configured to convert the longitudinal motion from the first and second piezoelectric stack to the combined longitudinal-torsional motion of the transducer;
a horn coupled to the piezoelectric stack opposite the inhomogeneous resonator, such that the piezoelectric stack is sandwiched between the horn and the inhomogeneous resonator, and wherein the horn has a first resonator cross section distal to the piezoelectric stack that is smaller than a second resonator cross section proximal to the first resonator cross section; and
an end effector coupled to the horn, wherein the end effector couples torsional mode vibrations produced by the inhomogeneous resonator or longitudinal mode vibrations to a solid or fluid medium.

2. The transducer system of claim 1, wherein the transducer system selectably operates in a torsional mode or a longitudinal-torsional mode, wherein the mode is selectable by selecting a first operating frequency or a second operating frequency.

3. The piezoelectric transducer system of claim 1, further comprising one or more grooves in a surface region of the system for mounting or holding the transducer system in a housing.

4. The piezoelectric transducer system of claim 1, further comprising a housing at least partially surrounding the piezoelectric stack.

5. The piezoelectric transducer system of claim 4, further comprising a spring biased between the groove and the housing.

6. The piezoelectric transducer system of claim 5, wherein the spring is a metal coil spring.

7. The piezoelectric transducer system of claim 5, wherein the spring is a canted circularly wound coil spring.

8. The piezoelectric transducer system of claim 5, wherein the spring is encapsulated in an elastomer or plastic material.

9. A piezoelectric transducer system comprising:
a transducer assembly, the transducer assembly comprising a back-mass, a piezoelectric stack, and a horn, the transducer assembly having a length of one-half wavelength of the transducer assembly's fundamental vibrational mode, wherein the piezoelectric stack comprises two or more piezoelectric elements;
wherein the back-mass includes an inhomogeneous resonator portion coupled to the piezoelectric stack, wherein the inhomogeneous resonator portion comprises a twisted bar configured to convert the longitudinal motion from the first and second piezoelectric stack to the combined longitudinal-torsional motion of the transducer;
wherein the horn is coupled to the piezoelectric stack opposite the back-mass, such that the piezoelectric stack is sandwiched between the horn and the back-mass, and wherein the horn has a first resonator cross section distal to the piezoelectric stack that is smaller than a second resonator cross section proximal to the first resonator cross section; and
an end effector coupled to the horn, wherein the end effector couples torsional mode vibrations produced by the inhomogeneous resonator or longitudinal mode vibrations to a solid or fluid medium.

10. The transducer system of claim 9, wherein the transducer system selectably operates in a torsional resonant mode or a longitudinal-torsional resonant mode, wherein the resonant mode is selectable by selecting a first operating frequency or a second operating frequency.

11. The piezoelectric transducer system of claim 10, further comprising one or more grooves in a surface region of the system for mounting or holding the transducer system in a housing.

12. The piezoelectric transducer system of claim 11, further comprising a housing.

13. The piezoelectric transducer system of claim 12, further comprising a spring biased between the groove and the housing.

14. The piezoelectric transducer system of claim 13, wherein the spring is a metal coil spring.

15. The piezoelectric transducer system of claim 13, wherein the spring is a canted circularly wound coil spring.

16. The piezoelectric transducer system of claim 13, wherein the spring is encapsulated in an elastomer or plastic material.

17. A piezoelectric transducer system comprising:
a transducer assembly, the transducer assembly comprising a back-mass, a piezoelectric stack, and a horn, the transducer assembly having a length of one-half wavelength of the transducer assembly's fundamental vibrational mode, wherein the piezoelectric stack comprises two or more piezoelectric elements;
wherein the back-mass includes an inhomogeneous resonator portion coupled to the piezoelectric stack, wherein the inhomogeneous resonator portion comprises a twisted bar configured to convert the longitudinal motion from the first and second piezoelectric stack to the combined longitudinal-torsional motion of the transducer;
wherein the horn is coupled to the piezoelectric stack opposite the back-mass, such that the piezoelectric stack is sandwiched between the horn and the back-mass, and wherein the horn has a first resonator cross section distal to the piezoelectric stack that is smaller than a second resonator cross section proximal to the first resonator cross section; and an end effector coupled to the horn, wherein the end effector couples torsional mode vibrations produced by the inhomogeneous resonator or longitudinal mode vibrations to a solid or fluid medium;

wherein the transducer assembly and end-effector comprise a central opening substantially along the longitudinal axis of the transducer assembly.

18. The piezoelectric transducer system of claim 17, wherein the central opening is configured to provide aspiration of particles from the solid or fluid medium.

* * * * *